United States Patent
Lin et al.

(10) Patent No.: US 11,839,635 B1
(45) Date of Patent: Dec. 12, 2023

(54) **METHOD AGAINST *SALMONELLA TYPHIMURIUM* INFECTION WITH SYMBIOTIC COMPOSITION**

(71) Applicant: SYNBIO TECH INC., Kaohsiung (TW)

(72) Inventors: Shih-Hsuan Lin, Kaohsiung (TW); Ai-Hua Hsu, Kaohsiung (TW); Chia-Chia Lee, Kaohsiung (TW)

(73) Assignee: SYNBIO TECH INC., Kaohsiung (TW)

( * ) Notice: Subject to any disclaimer, the term of this patent is extended or adjusted under 35 U.S.C. 154(b) by 0 days.

(21) Appl. No.: 17/955,287

(22) Filed: Sep. 28, 2022

(51) Int. Cl.
*A61K 35/747* (2015.01)
*A61P 31/04* (2006.01)
*A61K 35/744* (2015.01)

(52) U.S. Cl.
CPC .......... *A61K 35/747* (2013.01); *A61K 35/744* (2013.01); *A61P 31/04* (2018.01)

(58) Field of Classification Search
CPC ...... A61K 35/747; A61K 35/744; A61P 31/04
See application file for complete search history.

(56) References Cited

U.S. PATENT DOCUMENTS

2020/0008437 A1* 1/2020 Huang ................. A23C 9/1203

OTHER PUBLICATIONS

J. Piatek et al., "Persistent infection by Salmonella enterica servovar Typhimurium: are synbiotics a therapeutic option?—a case report," Beneficial Microbes, 10(2), pp. 211-217, 2019, doi:10.3920/BM2018. 0080.

B. Duan et al., "Lactobacillus rhamnosus GG defense against Salmonella enterica serovar Typhimurium infection through modulation of M1 macrophage Polarization," Microbial Pathogenesis, 156, pp. 1-11, 2021, https://doi.org/10.1016/j.micpath.2021. 104939.

* cited by examiner

*Primary Examiner* — Louise W Humphrey
*Assistant Examiner* — Alexander M Duryee
(74) *Attorney, Agent, or Firm* — Hamre, Schumann, Mueller & Larson, P.C.

(57) ABSTRACT

A method against *Salmonella typhimurium* infection includes using a composition containing cultures of *Lactobacillus rhamnosus* LRH10 which is deposited at the Deutsche Sammlung von Mikroorganismen und Zellkulturen (DSMZ) GmbH under an accession number DSM 32786, *Lactobacillus paracasei* LPC12 which is deposited at the DSMZ GmbH under an accession number DSM 32785, *Lactobacillus fermentum* LF26 which is deposited at the DSMZ GmbH under an accession number DSM 32784, *Streptococcus thermophilus* ST30 which is deposited at the DSMZ GmbH under an accession number DSM 32788, and *Lactobacillus helveticus* LH43 which is deposited at the DSMZ GmbH under an accession number DSM 32787.

6 Claims, 1 Drawing Sheet

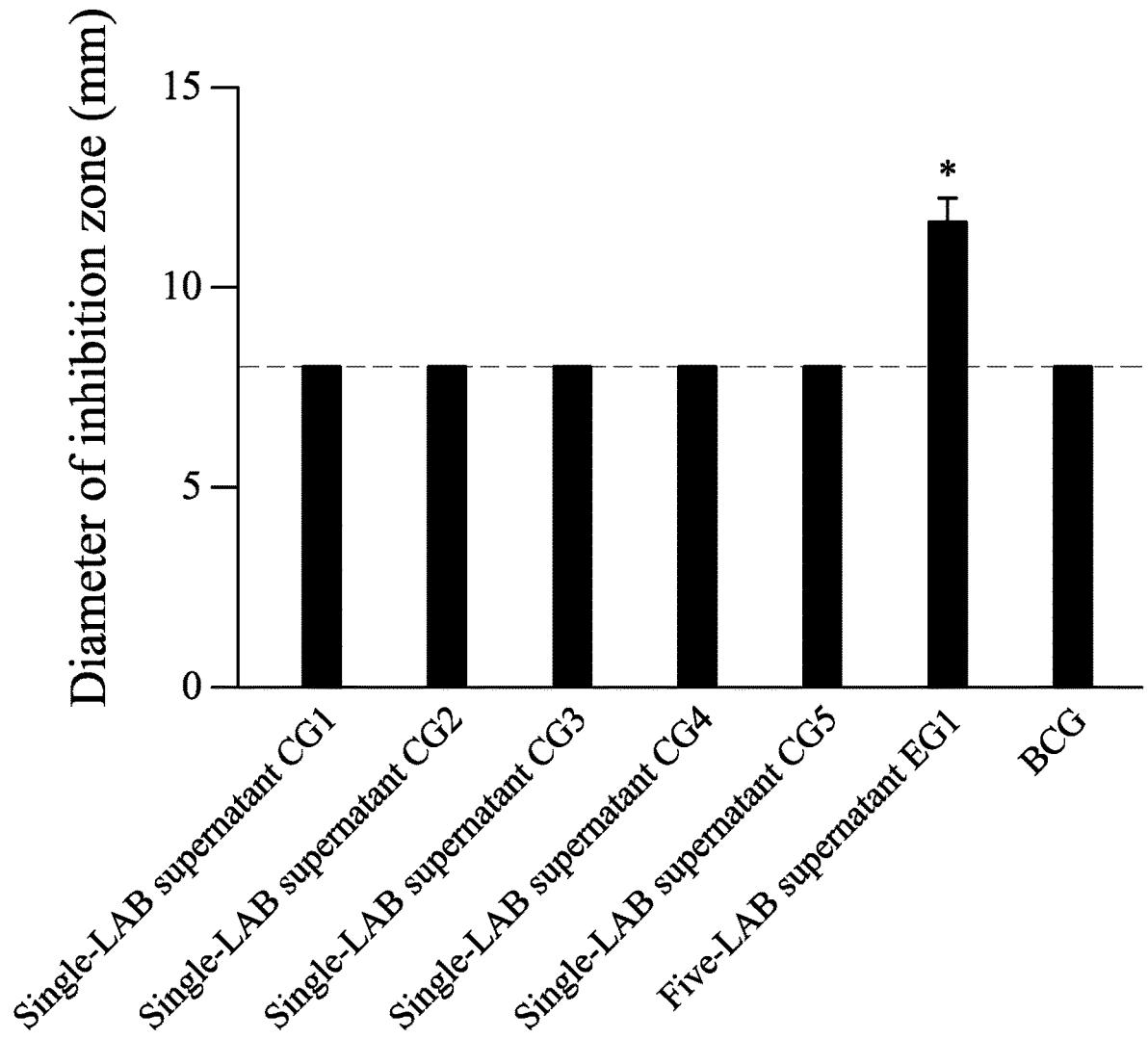

METHOD AGAINST *SALMONELLA TYPHIMURIUM* INFECTION WITH SYMBIOTIC COMPOSITION

FIELD

The present disclosure relates to a method against *Salmonella typhimurium* infection using a composition containing cultures of five lactic acid bacterial strains.

BACKGROUND

*Salmonella typhimurium* is a gram negative bacteria that colonizes the intestinal tract of animals (such as pigs or humans), and more particularly the ileum, caecum, and spiral colon, through their Peyer's patches. *Salmonella typhimurium* infection (also known as salmonellosis) may occur by ingestion of infected food sources, or from a contaminated environment, including the veterinary hospital. Major symptoms of salmonellosis include fever, anorexia, diarrhea, vomiting, and abdominal pain. *Salmonella typhimurium* most often causes gastroenteritis in humans.

Salmonellosis is typically treated with antibiotics (such as apramycin, ceftiofur, trimethoprim-sulfamethoxazole (TMP-SIM), and gentamicin). However, these antibiotics might cause *Salmonella typhimurium* to develop antibiotic resistance, and might cause severe side effects and adverse effects.

Probiotics are resident normal flora of the intestinal tract, and are believed to play important roles in regulating proper intestinal immunity and digestion by balancing intestinal microflora. These beneficial microorganisms are widely used as live microbial dietary supplements and can help to restore intestinal microflora balance. Many species of lactic acid bacteria (LAB) are conferred with the generally recognized as safe (GRAS) status, and are widely used as probiotics. Common LAB include *Lactobacillus* spp., *Lactococcus* spp., *Pediococcus* spp., *Streptococcus* spp., *Enterococcus* spp., *Bifidobacterium* spp., *Bacillus* spp., *Leuconostoc* spp., etc.

Previous studies have demonstrated that certain strains of LAB are effective against *Salmonella typhimurium* infection. For example, *Streptococcus thermophilus* St-21, *Lactobacillus helveticus* SP-27, and *Lactobacillus rhamnosus* GG have been demonstrated to inhibit the growth of *Salmonella typhimurium*, hence being capable of achieving the effect of anti-*Salmonella typhimurium* infection (J. Piatekl et al. (2019), *Beneficial Microbes*, 10(2):211-217 and Bingjie Duan et. al. (2021), *Microb Pathog.*, 156:104939).

In spite of the aforesaid, there is still a need to develop a new strategy that is effective against Salmonella typhimurium infection.

SUMMARY

Therefore, an object of the present disclosure is to provide a method against Salmonella typhimurium infection, which can alleviate at least one of the drawbacks of the prior art.

The method includes administering to a subject in need thereof a composition containing cultures of *Lactobacillus rhamnosus* LRH10 which is deposited at the Deutsche Sammlung von Mikroorganismen and Zellkulturen (DSMZ) GmbH under an accession number DSM 32786, *Lactobacillus paracasei* LPC12 which is deposited at the DSMZ GmbH under an accession number DSM 32785, *Lactobacillus fermentum* LF26 which is deposited at the DSMZ GmbH under an accession number DSM 32784, *Streptococcus thermophiles* ST3O which is deposited at the DSMZ GmbH under an accession number DSM 32788, and *Lactobacillus helveticus* LH43 which is deposited at the DSMZ GmbH under an accession number DSM 32787.

BRIEF DESCRIPTION OF THE DRAWINGS

Other features and advantages of the present disclosure will become apparent in the following detailed description of the embodiments with reference to the accompanying drawings, of which:

FIG. 1 shows the diameter of the inhibition zone determined in each group of Example 1, infra, in which the symbol "*" represents $p<0.05$ (compared with the single-LAB supernatant CG1 to CG5 and BCG).

DETAILED DESCRIPTION

It is to be understood that, if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the word "comprises" has a corresponding meaning.

Unless defined otherwise, all technical and scientific terms used herein have the meaning commonly understood by a person skilled in the art to which the present disclosure belongs. One skilled in the art will recognize many methods and materials similar or equivalent to those described herein, which could be used in the practice of the present disclosure. Indeed, the present disclosure is in no way limited to the methods and materials described.

The present disclosure provides a method against *Salmonella typhimurium* infection, which includes administering to a subject in need thereof a composition containing cultures of *Lactobacillus rhamnosus* LRH10 which is deposited at the Deutsche Sammlung von Mikroorganismen and Zellkulturen (DSMZ) GmbH under an accession number DSM 32786, *Lactobacillus paracasei* LPC12 which is deposited at the DSMZ GmbH under an accession number DSM 32785, *Lactobacillus fermentum* LF26 which is deposited at the DSMZ GmbH under an accession number DSM 32784, *Streptococcus thermophilus* ST30 which is deposited at the DSMZ GmbH under an accession number DSM 32788, and *Lactobacillus helveticus* LH43 which is deposited at the DSMZ GmbH under an accession number DSM 32787.

As used herein, the term "against *Salmonella typhimurium* infection" or "anti-*Salmonella typhimurium* infection" means prevention of infection by *Salmonella typhimurium*, suppression of *Salmonella typhimurium* replication, and/or treatment and/or prevention of infectious diseases caused by *Salmonella typhimurium*.

As used herein, the term "administering" or "administration" means introducing, providing or delivering the above-mentioned composition to a subject by any suitable routes to perform its intended function.

As used herein, the term "subject" refers to any animal of interest, such as humans, monkeys, hamsters, cows, sheep, horses, pigs, goats, dogs, cats, mice, and rats. In certain embodiments, the subject is a human.

According to the present disclosure, the culture of each lactic acid bacterial strain may be prepared by culturing the abovementioned lactic acid bacterial strain in a liquid or solid medium suitable for growth and/or proliferation thereof.

In certain embodiments, the culture of each lactic acid bacterial strain may be prepared by culturing the abovementioned lactic acid bacterial strain in an amount of $10^5$ cFU/mL to $10^9$ CFU/mL in a liquid or solid medium suitable for growth thereof. In an exemplary embodiment, the abovementioned lactic acid bacterial strain is cultivated in an amount of 106 CFU/mL to $10^8$ CFU/mL in a liquid or solid medium suitable for growth thereof.

As used herein, the term "culturing" can be used interchangeably with other terms such as "fermentation" and "cultivation".

The procedures and conditions for culturing the lactic acid bacterial strain may be adjusted according to practical requirements. In this regard, those skilled in the art may refer to journal articles, e.g., Kimoto-Nira H. et al. (2012), *J Dairy Sci.*, 95(4):2176-2185. doi: 10.3168/jds.2011-4824.

In certain embodiments, the liquid medium suitable for culturing the lactic acid bacterial strain is 10% skim milk.

In certain embodiments, the culture of each lactic acid bacterial strain is a liquid culture.

In certain embodiments, a number ratio of *Lactobacillus rhamnosus* LRH10, *Lactobacillus paracasei* LPC12, *Lactobacillus fermentum* LF26, *Streptococcus thermophiles* ST30, and *Lactobacillus helveticus* LH43 in the composition ranges from 5.1:29.7:1.9:47.8:1.2 to 10.9:41.3:3.4:53.2:5.7.

In an exemplary embodiment, the number ratio of *Lactobacillus rhamnosus* LRH10, *Lactobacillus paracasei* LPC12, *Lactobacillus fermentum* LF26, *Streptococcus thermophiles* ST30, and *Lactobacillus helveticus* LH43 in the composition is 7.8:35.5:2.6:50.4:3.3.

According to the present disclosure, the liquid culture may be substantially free of cells.

As used herein, the term "substantially free of" means that the liquid culture lacks a significant amount of a specified component (i.e., lactic acid bacterial cells). In certain embodiments, the amount of the lactic acid bacterial cells does not have a measurable effect on the properties of the liquid culture. In other embodiments, the liquid culture is completely free of the bacterial cells.

According to the present disclosure, the liquid culture which is substantially free of cells is obtained by subjecting a culture formed after culturing the lactic acid bacterial strain to a separation treatment to remove bacterial cells therefrom.

According to the present disclosure, the separation treatment may be performed using techniques well-known to those skilled in the art. Examples of the separation treatment may include, but are not limited to, filtration, centrifugation (such as multi-stage centrifugation), concentration, and combinations thereof.

In an exemplary embodiment, the liquid culture which is substantially free of cells is obtained by subjecting the culture formed after culturing the lactic acid bacterial strain to a centrifugation treatment.

According to the present disclosure, the composition may be formulated as a food product using a standard technique well known to one of ordinary skill in the art. For example, the composition may be directly added to an edible material or may be used to prepare an intermediate composition (e.g., a food additive or a premix) suitable to be subsequently added to the edible material.

As used herein, the term "food product" refers to any article or substance that can be ingested by a subject into the body thereof. Examples of the food product may include, but are not limited to, milk powders, fermented milk, yogurt, butter, beverages (e.g., tea, coffee, etc.), functional beverages, a flour product, baked foods, confectionery, candies, fermented foods, animal feeds, health foods, infant foods, and dietary supplements.

According to the present disclosure, the composition may be prepared in the form of a pharmaceutical composition. The pharmaceutical composition may be formulated into a dosage form suitable for oral, parenteral or topical administration using technology well known to those skilled in the art.

According to the present disclosure, the dosage form suitable for oral administration includes, but is not limited to, sterile powders, tablets, troches, lozenges, pellets, capsules, dispersible powders or granules, solutions, suspensions, emulsions, syrup, elixir, slurry, drops, and the like.

For parenteral administration, the pharmaceutical composition according to the present disclosure may be formulated into an injection, e.g., a sterile aqueous solution or a dispersion.

The pharmaceutical composition according to the present disclosure may be administered via one of the following parenteral routes: intraperitoneal injection, intrapleural injection, intramuscular injection, intravenous injection, intraarterial injection, intraarticular injection, intrasynovial injection, intrathecal injection, intracranial injection, intraepidermal injection, subcutaneous injection, intradermal injection, intralesional injection, and sublingual administration. In certain embodiments, the pharmaceutical composition may be administered via intravenous injection.

According to the present disclosure, the pharmaceutical composition may be formulated into an external preparation suitable for topical application to the skin using technology well known to those skilled in the art. The external preparation includes, but is not limited to, emulsions, gels, ointments, creams, patches, liniments, powder, aerosols, sprays, lotions, serums, pastes, foams, drops, suspensions, salves, and bandages.

The pharmaceutical composition according to the present disclosure may further include a pharmaceutically acceptable carrier widely employed in the art of drug-manufacturing. For instance, the pharmaceutically acceptable carrier may include one or more of the following agents: solvents, buffers, emulsifiers, suspending agents, decomposers, disintegrating agents, dispersing agents, binding agents, excipients, stabilizing agents, chelating agents, diluents, gelling agents, preservatives, fillers, wetting agents, lubricants, absorption delaying agents, liposomes, and the like. The choice and amount of the aforesaid agents are within the expertise and routine skills of those skilled in the art.

The dose and frequency of administration of the composition according to the present disclosure may vary depending on the following factors: the severity of the illness or disorder to be treated, routes of administration, and age, physical condition and response of the subject to be treated. In general, the composition may be administered in a single dose or in several doses.

The disclosure will be further described by way of the following examples. However, it should be understood that the following examples are solely intended for the purpose of illustration and should not be construed as limiting the disclosure in practice.

EXAMPLES

General Experimental Materials

1. Lactic Acid Bacterial (LAB) Strains

Five LAB strains, i.e., *Lactobacillus rhamnosus* LRH10, *Lactobacillus paracasei* LPC12, *Lactobacillus fermentum*

LF26, *Streptococcus thermophiles* ST30, and *Lactobacillus helveticus* LH43 (which are disclosed in US 2020/0008437 A1 and are readily available to the public) have been deposited at the Deutsche Sammlung von Mikroorganismen and Zellkulturen (DSMZ) GmbH (Inhoffenstraβe 7B, 38124 Braunschweig, Germany) in accordance with the Budapest Treaty.

The relevant information regarding each of the LAB strains (including accession number and date of deposit) is listed in Table 1 below.

TABLE 1

| LAB strains | Accession number | Date of deposit |
|---|---|---|
| *Lactobacillus rhamnosus* LRH10 | DSM 32786 | Apr. 3, 2018 |
| *Lactobacillus paracasei* LPC12 | DSM 32785 | Apr. 3, 2018 |
| *Lactobacillus fermentum* LF26 | DSM 32784 | Apr. 3, 2018 |
| *Streptococcus thermophilus* ST30 | DSM 32788 | Apr. 3, 2018 |
| *Lactobacillus helveticus* LH43 | DSM 32787 | Apr. 3, 2018 |

2. *Salmonella Typhimurium* Used in the Following experiments was isolated from the intestines of chickens by the applicant.

General Experimental Procedures

1. Statistical Analysis

All the experiments described below were performed in triplicates. The experimental data of all the test groups are expressed as mean±standard deviation (SD), and were analyzed using one-way analysis of variance (ANOVA) followed by Tukey-Kramer test, so as to evaluate the differences between the groups. Statistical significance is indicated by $p<0.05$.

Example 1

Evaluation for the Effect of Liquid Culture of LAB Strain According to this Disclosure Against *Salmonella typhimurium*

Experimental Procedures

A. Preparation of cell culture supernatant of LAB strain

A respective one of *Lactobacillus rhamnosus* LRH10, *Lactobacillus paracasei* LPC12, *Lactobacillus fermentum* LF26, and *Lactobacillus helveticus* LH43 described in section 1 of "General Experimental Materials" was inoculated in a Difco™ Lactobacilli MRS (De Man, Rogosa and Sharpe) broth (Cat. No. 288130, BD Difco), while *Streptococcus thermophilus* ST30 described in section 1 of "General Experimental Materials" was inoculated in a M17 broth (HiMedia®). The respective one of the five LAB strains was cultivated in an incubator (37° C.) under an aerobic condition for 16 hours to obtain a respective inoculum.

Next, the respective inoculum was inoculated in an amount of 2% (v/v) into 10% skim milk, followed by subculturing in an incubator (37° C.) under an aerobic condition for 16 hours, so as to obtain a single-LAB liquid culture of the respective LAB strain. In addition, the inoculums of *Lactobacillus rhamnosus* LRH10, *Lactobacillus paracasei* LPC12, *Lactobacillus fermentum* LF26, *Streptococcus thermophilus* ST30, and *Lactobacillus helveticus* LH43 were inoculated into 10% skim milk (Acumedia®) in a volume ratio of 1:1:1:1:1 (the amount of the respective inoculum was 0.4% (v/v)), followed by subculturing in an incubator (37° C.) under an aerobic condition for 16 hours, so as to obtain a five-LAB liquid culture. The number of the respective LAB strain in the five-LAB liquid culture was counted using techniques well-known to those skilled in the art. The result showed that the number ratio of *Lactobacillus rhamnosus* LRH10, *Lactobacillus paracasei* LPC12, *Lactobacillus fermentum* LF26, *Streptococcus thermophilus* ST30, and *Lactobacillus helveticus* LH43 in the five-LAB liquid culture was 7.8:35.5:2.6:50.4:3.3.

Thereafter, a respective one of the five single-LAB liquid cultures and the five-LAB liquid culture was subjected to centrifugation at 5,000 rpm for 10 minutes, the resultant cell culture supernatant was collected to be used in the following experiments.

B. Determination of antibacterial activity against *Salmonella typhimurium*

Each of the five cell culture supernatants obtained from the five single-LAB liquid cultures as described in section A above served as a single-LAB supernatant group, i.e., a corresponding one of single-LAB supernatant comparative groups 1 to 5 (abbreviated as single-LAB supernatant CG1 to CG5) as shown in Table 2 below. In addition, the cell culture supernatant obtained from the five-LAB liquid culture as described in section A above served as a five-LAB supernatant group, i.e., a five-LAB supernatant experimental group 1 (abbreviated as five-LAB supernatant EG1) as shown in Table 2 below. Moreover, 10% skim milk was used as a blank control group (BCG).

TABLE 2

| Group | LAB strain |
|---|---|
| Single-LAB supernatant CG1 | *Lactobacillus rhamnosus* LRH10 |
| Single-LAB supernatant CG2 | *Lactobacillus paracasei* LPC12 |
| Single-LAB supernatant CG3 | *Lactobacillus fermentum* LF26 |
| Single-LAB supernatant CG4 | *Streptococcus thermophilus* ST30 |
| Single-LAB supernatant CG5 | *Lactobacillus helveticus* LH43 |
| Five-LAB supernatant EG1 | *Lactobacillus rhamnosus* LRH10, *Lactobacillus paracasei* LPC12, *Lactobacillus fermentum* LF26, *Streptococcus thermophilus* ST30, and *Lactobacillus helveticus* LH43 |
| BCG | — |

*Salmonella typhimurium* described in section 2 of "General Experimental Materials" was inoculated in a tryptic soy broth (TSB) (HiMedia®), and was then cultivated in an incubator (37° C.) under an aerobic condition for 16 hours. After centrifugation at 5,000 rpm and room temperature for 10 minutes, the resultant cell pellet was collected. The cell pellet was then washed with 5 ml of Dulbecco's phosphate buffered saline (DPBS, pH 7.39) (Thermo Scientific™) for 2 times, followed by suspending in DPBS, so as to obtain a bacterial suspension having a bacterial concentration of $10^9$ CFU/mL. The bacterial suspension was then mixed with a suitable amount of a 0.85% sterile saline solution, so as to obtain a bacterial solution having a bacterial concentration of $10^7$ CFU/mL (prepared using a dilution factor of $10^2$).

Thereafter, 100 µL of the bacterial solution was added to a TSB agar plate, followed by adding sterile small glass beads, and then the TSB agar plate was shook so that the bacterial solution was evenly distributed on the TSB agar medium. Next, the small glass beads were poured out, and a sterile pipette tip (size: 9.25 mm) was used to create 7 holes on the TSB agar medium. Thereafter, 100 µL of the respective one of the single-LAB supernatant CG1 to CG5, the five-LAB supernatant EG1, and the BOG was added into different holes of the TSB agar medium, followed by cultivation in an incubator (37° C.) under an aerobic condition for 16 hours.

The diameter of the inhibition zone of each group was determined using techniques well-known to those skilled in the art. The data thus obtained were analyzed according to the method described in section 1 of "General Experimental Procedures".

Results

FIG. 1 shows the diameter of the inhibition zone determined in each group. As shown in FIG. 1, the diameter of the inhibition zone determined in the five-LAB supernatant EG1 was higher than those determined in the single-LAB supernatant CG1 to CG5.

These results suggest that the cell culture supernatant obtained by co-cultivation of Lactobacillus rhamnosus LRH10, Lactobacillus paracasei LPC12, Lactobacillus fermentum LF26, *Streptococcus thermophilus* ST30, and *Lactobacillus helveticus* LH43 can exhibit satisfactory efficacy in inhibiting growth of *Salmonella typhimurium*.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A method for treating *Salmonella typhimurium* infection, comprising administering to a subject in need thereof a composition containing cultures of *Lactobacillus rhamnosus* LRH10 which is deposited at the Deutsche Sammlung von Mikroorganismen and Zellkulturen (DSMZ) GmbH under an accession number DSM 32786, *Lactobacillus paracasei* LPC12 which is deposited at the DSMZ GmbH under an accession number DSM 32785, *Lactobacillus fermentum* LF26 which is deposited at the DSMZ GmbH under an accession number DSM 32784, *Streptococcus thermophilus* ST30 which is deposited at the DSMZ GmbH under an accession number DSM 32788, and *Lactobacillus helveticus* LH43 which is deposited at the DSMZ GmbH under an accession number DSM 32787.

2. The method as claimed in claim 1, wherein each of the cultures is a liquid culture.

3. The method as claimed in claim 2, wherein a ratio of colony forming units (CFU) of *Lactobacillus rhamnosus* LRH10, *Lactobacillus paracasei* LPC12, *Lactobacillus fermentum* LF26, *Streptococcus thermophilus* ST30, and *Lactobacillus helveticus* LH43 in the composition ranges from 5.1:29.7:1.9:47.8:1.2 to 10.9:41.3:3.4:53.2:5.7.

4. The method as claimed in claim 1, wherein the composition is formulated as a food product.

5. The method as claimed in claim 1, wherein the composition is formulated as a pharmaceutical composition.

6. The method as claimed in claim 5, wherein the pharmaceutical composition is in a dosage form selected from the group consisting of an oral dosage form, a parenteral dosage form, and a topical dosage form.

* * * * *